United States Patent [19]

Dyroff et al.

[11] Patent Number: 4,502,923

[45] Date of Patent: Mar. 5, 1985

[54] PRODUCTION OF HIGH PURITY ALKYL GLYOXYLATE BY PLURAL STAGE DISTILLATION

[75] Inventors: David R. Dyroff, Creve Coeur; Yueting Chou, Chesterfield; Dario R. Cova, Kirkwood, all of Mo.

[73] Assignee: Monsanto Company, St. Louis, Mo.

[21] Appl. No.: 539,506

[22] Filed: Oct. 6, 1983

[51] Int. Cl.³ .......................... B01D 3/10; C07C 69/66
[52] U.S. Cl. ........................................ 203/71; 203/14; 203/73; 203/80; 560/177
[58] Field of Search ...................... 203/14, 71, 73, 18, 203/80, 91, DIG. 21, 98, 77; 560/176, 177, 180; 562/577

[56] References Cited

U.S. PATENT DOCUMENTS

| | | | |
|---|---|---|---|
| 1,614,195 | 1/1927 | Haussler | 560/174 |
| 3,681,204 | 8/1972 | Mercier | 203/14 |
| 3,872,166 | 3/1975 | Spaenig et al. | 562/577 |
| 4,009,188 | 2/1977 | Heim et al. | 203/80 |
| 4,340,748 | 7/1982 | Baltes et al. | 560/177 |

FOREIGN PATENT DOCUMENTS 0153575  9/1983  Japan ........................ 203/91

OTHER PUBLICATIONS

J. Amer. Chem. Soc., W. Oroshnik et al., The Electrolytic Preparation of Ethyl Glyoxylate, 1941, 63, 3338.
Derwent Abstracts 05763, Week J49, E17, Japanese 57 176-929.

Primary Examiner—Wilbur Bascomb
Assistant Examiner—Virginia Manoharan
Attorney, Agent, or Firm—R. C. Griesbauer; J. C. Logomasini; A. H. Cole

[57] ABSTRACT

High purity alkyl glyoxylate is produced from complex mixtures containing alkyl glyoxylate, alkyl glycolate, water, alcohol and miscellaneous impurities. High purity alkyl glyoxylate is useful in the synthesis of alkyl glyoxylate polymers.

20 Claims, No Drawings

PRODUCTION OF HIGH PURITY ALKYL GLYOXYLATE BY PLURAL STAGE DISTILLATION

BACKGROUND OF THE INVENTION

This invention relates to the production of high purity alkyl glyoxylate. More particularly, the invention relates to the production of high purity alkyl glyoxylate from mixtures containing alkyl glyoxylate, alkyl glycolate, water, alcohol and miscellaneous impurities.

High purity alkyl glyoxylate is important as an intermediate for synthesis of other compounds, for example, alkyl glyoxylate polymers. (U.S. Pat. No. 4,144,226 issued Mar. 13, 1979 to M. M. Crutchfield et al). For its use in production of alkyl glyoxylate polymers, it is particularly important that the content of alkyl glycolate, water and alcohol be low enough to avoid excessively low average chain length in the polymer.

The prior art discloses methods for producing alkyl glyoxylate by the oxidation or dehydrogenation of alkyl glycolate to alkyl glyoxylate. See for Example U.S. Pat. No. 1,614,195 issued Jan. 11, 1927 to Alfred Haussler and U.S. Pat. No. 4,340,748 issued July 20, 1982 to Herbert Baltes et al.

These prior art methods for producing alkyl glyoxylate are conducted in the gaseous state and are represented by the following reaction (1).

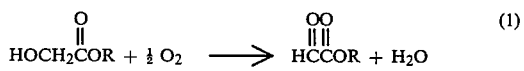

In this reaction (1) the conversion of alkyl glycolate to alkyl glyoxylate is not complete and the product of the reaction contains in addition to the alkyl glyoxylate, unconverted alkyl glycolate, water, alcohol which is produced by side reactions or derived from the alkyl glycolate feed, and miscellaneous impurities. Following condensation and recovery of such mixtures, some or all of the contained alkyl glyoxylate is present in chemically combined forms such as alkyl glyoxylate hydrate, alkyl glyoxylate oligomers, and various hemiacetals of alkyl glyoxylate. To obtain high purity alkyl glyoxylate an additional process is required to convert the hydrate or hemiacetal to alkyl glyoxylate per se. Such conversion is made very difficult by the very complex interreactions of the components of the mixture under distillation conditions which limit both the purity of the alkyl glyoxylate and its recovery per pass. In the prior art, this conversion has been accomplished by treatment with $P_2O_5$ followed by distillation to liberate the alkyl glyoxylate (W. Oroshnik and P. E. Spoerri, J. Amer. Chem. Soc. 1941, 63,3338). While this method is effective, it suffers several serious disadvantages. Large amounts of $P_2O_5$ are consumed, which adds considerably to the cost of production of high purity alkyl glyoxylate. Also, alcohol liberated from the hemiacetals is consumed by reaction with the $P_2O_5$ and thus cannot be conveniently recovered in a suitable form for reuse in the production of alkyl glycolate and/or alkyl glyoxylate. Furthermore, the reaction with $P_2O_5$ is highly exothermic and can be difficult to control under some conditions.

It is apparent that there is a need for a more efficient method for producing high purity alkyl glyoxylate from mixtures containing alkyl glyoxylate, alkyl glycolate, water, alcohol and miscellaneous impurities. One advantage of the present invention is that it provides such a process which avoids consumption of $P_2O_5$ or other such reagents and which recovers liberated alcohol for reuse. A further advantage of the present process is production of much higher product purity with higher conversion per pass than can be obtained using conventional distillation techniques without the use of $P_2O_5$.

SUMMARY OF THE INVENTION

These and other advantages are achieved by a series of distillations of a mixture containing alkyl glyoxylate, alkyl glycolate, water, alcohol and miscellaneous impurities, said mixture having an alkyl glycolate/alkyl glyoxylate molar ratio greater than about 1.0, which comprises (a) reducing the water and alcohol content by distilling the mixture at reduced pressure to provide a residue mixture having a combined water and alcohol content of less than about 1% by weight;

(b) where the residue mixture has an alkyl glycolate/alkyl glyoxylate molar ratio greater than about 1.5, reducing the alkyl glycolate content by distilling the residue mixture at a lower pressure to provide a residue mixture having an alkyl glycolate/alkyl glyoxylate molar ratio in the range of about 1.0 to about 1.4;

(c) distilling the residue mixture at increased pressure and recovering high purity alkyl glyoxylate as the distillate.

As used herein, the terms alkyl glyoxylate, alkyl glycolate, alcohol and water characterizing the mixture employed in accordance with this invention includes their respective content in chemically combined forms, such as alkyl glyoxylate hydrate, alkyl glyoxylate oligomer, alkyl glyoxylate-alkyl hemiacetal and alkyl glyoxylate-alkyl glycolate hemiacetal, present in the mixture.

The alkyl moieties of the alkyl glyoxylate, alkyl glycolate and alcohol can be like or unlike. Preferably, the alkyl moieties are all the same and are alkyl of 1 to 4 carbon atoms. Particularly preferred is methyl.

DETAILED DESCRIPTION OF THE INVENTION

In accordance with the present invention, high purity alkyl glyoxylate is obtained from a complex mixture containing alkyl glyoxylate, alkyl glycolate, alcohol, water and miscellaneous impurities by a series of distillations under controlled conditions. The relative amounts of the components present in the starting mixture can vary widely provided that the alkyl glycolate/alkyl glyoxylate molar ratio (hereinafter referred to as Gc/Gx) is or is adjusted to at least about 1.0. Although the components are present in various chemically combined forms, the amount of each component contained in the mixture utilized in the present process is determined by conventional analytical procedures using vapor phase chromatography.

It has been found that high purity alkyl glyoxylate can be obtained from such mixtures by: removing the low boilers by distilling the mixture at reduced pressure in the range of about 50 to about 300 torr (6.7–40.0 kPa) to reduce the combined water and alcohol content of the mixture to less than about 1% by weight; removing any excess alkyl glycolate by distilling the residue mixture at lower pressure, less than about 35 torr (4.7 kPa) to reduce the Gc/Gx of the residue mixture to about 1.0 to about 1.4 and distilling the residue mixture at increased pressure of at least about 600 torr (80.0 kPa) to obtain the alkyl glyoxylate as distillate.

In the low boiler removal step, the Gc/Gx of at least 1.0 shifts the equilibrium of the chemically combined forms of alkyl glyoxylate to allow adequate removal of water and low boiling alcohol from the mixture. The alcohol can be recovered in suitable form for recycle to the process for making esters of glycolic acid and the like.

It has been found that as the Gc/Gx is increased, a greater percentage of the glyoxylate is incorporated into alkyl glyoxylate-alkyl glycolate hemiacetal which lowers the percentages of water and alcohol which are incorporated into hydrates and hemiacetals. To remove sufficient water and alcohol from the complex mixture without significant loss of alkyl glyoxylate, the Gc/Gx must be at least about 1.0. As the Gc/Gx is increased further, water and alcohol are removed more completely. However, extremely high levels of Gc/Gx are not desirable in view of the overall efficiency of the process. A preferred range for the Gc/Gx is about 1.0 to about 3.5 and the range of about 1.5 to about 2.6 is particularly preferred. Particularly advantageous results are achieved where the Gc/Gx is about 2.4.

More complete removal of water and alcohol is achieved as pressure near the bottom of the low boiler distillation column is reduced. Lower pressure at the bottom of the column can be accomplished by lowering the pressure at the top of the column and/or by adjusting the column design and conditions for low pressure drop through the column. Advantageous results are achieved in the pressure range of about 50 to about 300 torr (6.7–40.0 kPa), with 150–200 torr (20.0–26.7 kPa) being especially preferred.

In the low boiler removal step, it is important to avoid excessive losses of alkyl glycolate and/or alkyl glyoxylate by codistillation with the low boilers leaving the top of the column. Minimizing such losses is accomplished by providing a sufficiently high number of theoretical stages and sufficiently high reflux ratio in the design of the column. The number of stages and reflux ratio required to reduce the losses can be determined by routine experimentation in view of the present description.

In continuous operations, it can be advantageous to include one or more side draws in the design of the low boiler removal column. For example, where methanol is present in the starting mixture, and all other components are higher boiling, it is advantageous to recover high purity methanol at the top of the column while removing all other low boilers along with a small amount of methanol at a side draw located between the feed point and the top of the column. Similarly, removal of high boilers might be accomplished at the bottom of the column with the glycolate and the glyoxylate being recovered at a side draw located between the feed point and the bottom of the column.

In the glycolate removal step, nearly pure alkyl glycolate can be distilled overhead and the composition of the bottom fraction approaches that of an equimolar mixture of glycolate and glyoxylate predominantly in the form of the alkyl glyoxylate alkyl glycolate hemiacetal. Sufficient glycolate removal to allow efficient operation of the subsequent alkyl glyoxylate recovery step has been achieved when the residue mixture, i.e., bottom fraction, has a Gc/Gx in the range of about 1.0 to about 1.4, preferably in the range of about 1.1 to about 1.3. Although some codistillation of alkyl glyoxylate occurs in this step, generally the overhead fraction has a Gc/Gx greater than 4.0, which makes it acceptable for recycle to the low boiler removal step. A portion of the minor amounts of water and alcohol of the residue mixture employed for the alkyl glycolate removal step is generally removed with the distillate, however, a portion remains in the bottom fraction due to hydrate and hemiacetal formation.

The separation of the alkyl glycolate is achieved at low pressures. It has been found that with low pressures the resulting lower temperatures shift the equilibrium toward a higher level of hemiacetal and a lower level of free alkyl glyoxylate, as well as slowing down the rate of hemiacetal dissociation. A pressure not exceeding about 35 torr at the bottom of the column is preferred and it is advantageous to have a low pressure drop through the column. A low pressure drop packed column is preferred over a sieve tray column which generally gives a much higher pressure drop. At very low pressures such as about 2 torr (0.27 kPa), a single stage evaporator can be employed for the separation of the glycolate. Particularly preferred are pressures in the range of from about 2 to about 22 torr (0.27–2.93 kPa) for the separation of the glycolate. As the pressure employed within the preferred range increases, more separation stages are required. However, if the reflux ratio and/or number of stages are excessively increased in the column, excessive pressure at the bottom of the column reduces the degree of separation of the alkyl glycolate. In general, the selection of both equipment and reflux ratio employed in the glycolate removal step will be a matter of overall process efficiency that can be determined by routine experimentation in view of the present description.

In the alkyl glyoxylate recovery step, distillation of the resultant mixture of the glycolate removal step is conducted at increased pressures in the range of about 600 to about 1550 torr (80.0–206.6 kPa) or more. A particularly preferred pressure range is about 700 to about 912 torr (93.3–121.6 kPa).

Using pressures in the range of 700 to about 912 torr, recovery of alkyl glyoxylate as distillate is sufficiently complete to achieve a Gc/Gx in the bottom fraction of about 4.0. At lower pressures, recovery of high purity alkyl glyoxylate is less complete, and it is difficult to prevent leakage of small amounts of air into the distillation system which is especially harmful in this step of the process. Also, as pressure is decreased the temperature of the high purity glyoxylate near the top of the column and in the condenser drops, which increases the danger of equipment pluggage caused by accumulation of viscous alkyl glyoxylate polymer. At pressures greater than the desired range, the resulting high temperatures cause significant amounts of side reactions to occur reducing the yield and purity of the alkyl glyoxylate.

In the alkyl glyoxylate recovery step, sufficient reflux and number of stages are provided to achieve optimum separation of the alkyl glyoxylate from the mixture at the selected operating pressure. These parameters can be determined by routine experimentation in view of the present description. A portion of the minor amounts of water and alcohol entering the alkyl glyoxylate recovery step is generally retained in the bottom fraction due to hydrate and hemiacetal formation. In continuous distillation, under some conditions some rejection of water, alcohol and other low boilers can also be accomplished at the top of the column by the use of a partial condenser or by removing the alkyl glyoxylate product as a side draw between the feed point and the top of the column. In a batch distillation, the same thing can be accomplished by removing some of the initial distillate for recycle.

Some rejection of high boiling impurities may be desirable at the bottom of the alkyl glyoxylate recovery column for such purposes as preventing excessive acidity in the recycle stream. This can be accomplished in a number of ways such as a split reboiler, a side draw near the bottom, a purge stream with or without recovery of its contained alkyl glycolate and alkyl glyoxylate, etc. Rejected high boiler can be used as a fuel.

Acidity in the process streams, due to acidic impurities which can increase upon continued heating or recycle due to side reactions, increases the rate of equilibration among hemiacetals, hydrates, oligomers and their components. Excessive acidity is most likely to cause problems in the glycolate removal step. Acidity buildup can be reduced by using shorter residence times, lower temperatures, more high boiler removal, less acidic starting materials, etc.

In addition to the high purity alkyl glyoxylate stream produced by this process, a number of other streams are produced and are recycled in order to obtain the best overall efficiency. The bottom fraction from the alkyl glyoxylate recovery step can be recycled to the feed of the low boiler removal step. The overhead stream from the glycolate removal step can be partly or totally recycled to the feed of the low boiler removal step to increase the Gc/Gx to the more desired range and any excess glycolate can be recycled to a process for conversion of alkyl glycolate to alkyl glyoxylate. The alcohol recovered overhead in the low boiler removal step can be recycled for use in production of alkyl glycolate or alkyl glyoxylate by esterification of the corresponding carboxylic acid.

The present process or any of its steps can be carried out either continuously or batchwise. Continuous distillation is preferred because residence times are much lower which results in smaller losses to side reactions and fewer problems with buildup of excessive acidity.

Exclusion of air is desirable in all the steps because of side reactions caused by exposure to oxygen. Alkyl glyoxylate is particularly sensitive to adverse effects of oxygen and exclusion of air is especially important in the alkyl glyoxylate recovery step.

While this process is particularly effective for producing alkyl glyoxylate from mixtures which contain alkyl glycolate as a result of the process in which alkyl glyoxylate is produced by dehydrogenation of alkyl glycolate, it can be advantageously applied to mixtures which initially contain no alkyl glycolate. In such a case, alkyl glycolate is added to facilitate a high degree of removal of water and/or alcohol from the mixture with alkyl glyoxylate.

This invention is further illustrated by, but not limited to, the following examples wherein all percentages and parts are by weight unless otherwise indicated. In the compositions given, contents of adducts such as hydrates, oligomers and hemiacetals are expressed as their separate components.

EXAMPLE I (a) A mixture containing 7.46% water, 12.78% methanol, 22.96% methyl glyoxylate (Gx), 55.90% methyl glycolate (Gc), and 0.90% miscellaneous impurities was fed continuously to a 30 sieve tray distillation column operated at 167 torr (22.3 kPa) pressure at the top of the column with a 2:1 external reflux ratio. The feed was introduced between tray 20 and tray 21 counting from the bottom, and heat input was adjusted (tray 10 distillate temp. 81° C.) so that little Gc or Gx reached the top of the column but further increase in heat input caused little or no further decrease in the contents of water and methanol in the bottom fraction. The column diameter was 2.54 cm, and the feed rate was 366.9 grams per hour, resulting in a pressure drop through the column of about 35 torr (4.7 kPa). The feed to the column was preheated to about 65° C., and air leaks into the system were minimized. After reaching steady state, the composition of the recovered distillate was 42.44% water, 55.70% methanol, 0% Gx, 1.20% Gc and 0.66% miscellaneous impurities. Some methanol was lost through the condenser. The composition of the bottom fraction was 0.23% water, 0.04% methanol, 28.41% Gx, 70.23% Gc, and 1.09% miscellaneous impurities. Combined recovery of Gc and Gx was about 98%.

This illustrates the low boiler removal step of the process of this invention, and in particular, it illustrates the high degree of removal of water and alcohol which can be achieved when operating at 202 torr (26.9 kPa) pressure at the bottom of the column with a Gc/Gx in the feed of about 2.4. Note that the small loss of Gc to the distillate could be reduced further by moving the feed point further from the top of the column.

(b) A mixture of about the same composition as the bottom fraction produced in part (a) of this example was used as the feed in the following run to illustrate the glycolate removal step of the process of this invention.

A mixture containing 0.34% water, 0.21% methanol, 30.54% Gx, 68.13% Gc, and 0.78% miscellaneous impurities was fed continuously to a single stage flash evaporator operated at 2 torr (0.26 kPa) pressure. Heat input was adjusted so that the Gc/Gx in the bottom fraction was reduced to about 1.14. The evaporator diameter was 2.54 cm, and the feed rate was 152.3 cm$^3$ per hour. Air leaks were minimized. The condenser coolant temperature was −20° C. After reaching steady state, the composition of the recovered distillate was 0.35% water, 0.19% methanol, 5.48% Gx, 93.50% Gc, and 0.48% miscellaneous impurities. Some methanol and water were lost through the condenser. The composition of the bottom fraction was 0.21% water, 0.12% methanol, 46.26% Gx, 52.66% Gc, and 0.75% miscellaneous impurities. Combined recovery of Gc and Gx was essentially quantitative.

(c) A mixture of about the same composition as the bottom fraction produced in part (b) of this example was used as the feed in the following run to illustrate the glyoxylate recovery step of the process of this invention.

A mixture containing 0.05% water, 0.36% methanol, 43.72% Gx, 53.44% Gc, and 2.43% miscellaneous impurities was fed continuously to a 75 sieve tray distillation column operated at about 760 torr (101.3 kPa) pressure at the top of the column with a 3.5:1 external reflux ratio. The feed was introduced between tray 45 and tray 46 counting from the bottom, and the heat input was adjusted (tray 65 distillated temp. 130° C.) so that little Gc reached the top of the column but the Gc/Gx in the bottom fraction did not drop below about 3.9. The column diameter was 2.54 cm, and the feed rate was 766.8 cm$^3$ per hour, resulting in a pressure drop through the column of about 67 torr (8.9 kPa). The feed to the column was preheated to about 136° C., and air leaks into the system were minimized. After reaching steady state, the composition of the recovered distillate was 0.12% water, 0.19% methanol, 97.39% Gx, 0.11% Gc, and 2.19% miscellaneous impurities. Some methanol and water were lost through the condenser. The composition of the bottom fraction was 0.01% water, 0.29% methanol, 19.78% Gx, 77.41% Gc, and 2.51% miscellaneous impurities. Combined recovery of Gc and Gx was essentially quantitative.

EXAMPLES II–IV

The procedure of Example I, Part (a) was repeated except that feeds of varying Gc/Gx ratio were employed. The result of this variation upon the content of water plus methanol in the bottom fraction is shown in the following tabulation.

| Example | Feed Gc/Gx | % H₂O + CH₃OH in Bottom Fraction |
|---|---|---|
| II | 2.34 | 0.28 |
| III | 1.49 | 1.01 |
| IV | 0.97 | 2.11 |

EXAMPLES V–VI

The procedure of Example I, Part (a) was repeated except that the pressure at the top of the distillation column was increased to about 760 torr (101.3 kPa). The results are shown in the following tabulation as Example V. Similarly, the procedure of Example IV was repeated except that the pressure at the top of the distillation column was decreased to about 50 torr (6.7 kPa). The results are shown in the following tabulation as Example VI. Results of Examples I and IV are also repeated in the tabulation for comparison. From these results it can be seen that for a given Gc/Gx more complete removal of water and methanol can be achieved as pressure is reduced.

| Example No. | Feed Gc/Gx | Pressure Torr (kPa) | % H₂O + CH₃OH in Bottom Fraction |
|---|---|---|---|
| V | 2.4 | 760 (101.3) | 2.15 |
| I | 2.4 | 167 (22.3) | 0.27 |
| IV | 0.97 | 166 (22.1) | 2.11 |
| VI | 0.97 | 50 (6.7) | 1.17 |

EXAMPLES VII–VIII

The procedure of Example I, Part (b) was repeated except that the operating pressure of the flash evaporator was varied. As operating pressure increased, the degree of separation achieved declined markedly as shown in the following tabulation. Note that for ideal separation between excess Gc and the Gc-Gx hemiacetal, the distillate would have Gc/Gx of infinity, and the bottom Gc/Gx would be 1.0.

| Example | Pressure, torr | Distillate Gc/Gx | Bottom GC/Gx |
|---|---|---|---|
| VII | 2 | 10.4 | 1.07 |
| VIII | 9.5 | 3.83 | 1.52 |

EXAMPLE IX

To further illustrate operation at a pressure higher than 2 torr (0.27 kPa) in the glycolate removal step of the process of this invention, a computer was used to estimate the degree of separation which could be achieved in a low pressure drop packed distillation column of eleven theoretical stages, ignoring kinetic effects. Vapor-liquid equilibrium data used in these calculations was obtained by extrapolation of experimental data obtained at a number of pressures in the range 65–1520 torr (8.7–202.6 kPa). Operating conditions and the estimated degree of separation are shown in the following tabulation.

| | |
|---|---|
| Number of theoretical stages | 11 |
| Feed tray, number from the bottom | 7 |
| Reflux ratio | 4 |
| Pressure at top of column, torr (kPa) | 35 (4.7) |
| Pressure at bottom of column, torr (kPa) | 40 (5.3) |
| Distillation rate/feed rate | 0.46 |
| Distillate GC/Gx | 6.52 |
| Bottom GC/Gx | 1.25 |

The actual separation achieved in such a column may differ somewhat from that calculated above due to kinetic effects and/or extrapolation errors, however, it is concluded on the basis of the above estimate that a degree of separation comparable to that of a single stage flash evaporator operated at 2 torr (0.27 kPa) pressure can be achieved at a substantially higher pressure, for example 20–35 torr (2.7–4.7 kPa) at the bottom of the column, by replacing the evaporator with a suitably designed low pressure drop packed distillation column.

EXAMPLE X

To illustrate the effect of pressure upon the glyoxylate recovery step in the process of this invention, the following tabulation gives for a series of pressures the approximate compositions at which the vapor and liquid compositions become identical at equilibrium. These compositions were estimated by correlating vapor-liquid equilibrium data obtained in a small version of a Gillespie still.

| Pressure torr (kPa) | % Gx Where Vapor and Liquid Compositions are Identical |
|---|---|
| 1520 (202.6) | 13% Gx |
| 760 (101.3) | 23% Gx |
| 400 (53.3) | 30% Gx |
| 165 (22.0) | 35% Gx |
| 65 (8.7) | 43% Gx |

The data indicates that recovery of methyl glyoxylate as distillate from a methyl glycolate, methyl glyoxylate mixture should become more complete as pressure increases, since the constant boiling mixture produced at the bottom of the column contains less glyoxylate. In actual distillations, this trend is indeed observed, although the limiting bottom composition may differ somewhat from the equilibrium value due to kinetic effects.

The foregoing description and examples demonstrate the production of high purity alkyl glyoxylate suitable as an intermediate for the synthesis of alkyl glyoxylate polymers. Preferably the alkyl glyoxylate useful as feed for polymerization contains at least 30 moles of alkyl glyoxylate per mole of water, alcohol and alkyl glycolate combined. Alkyl glyoxylate containing more than 30 moles alkyl glyoxylate per mole of water, alcohol and alkyl glycolate combined can be obtained in accordance with the present invention.

Although the invention has been described in terms of specific embodiments which are set forth in considerable detail, it should be understood that this is by way of illustration only and that the invention is not necessarily limited thereto since alternative embodiments and operating techniques will become apparent to those skilled in the art in view of the disclosure. Accordingly, modifications are contemplated which can be made without departing from the spirit of the described invention. For example use of a non-condensible gas purge within an evaporator or a distillation column can often be used to produce effects similar to those of reduced pressure, since this lowers the partial pressures of all the condensible components.

What is claimed is:

1. A process for production of high purity alkyl glyoxylate from a mixture containing alkyl glyoxylate, alkyl glycolate, water, alcohol and miscellaneous impurities, said mixture having an alkyl glycolate/alkyl glyoxylate molar ratio greater than about 1.0, which comprises:
   (a) reducing the water and alcohol content by distilling the mixture at a reduced pressure to provide a residue mixture having a combined water and alcohol content of less than about 1% by weight; where the residue mixture has an alkyl glycolate/alkyl glyoxylate molar ratio greater than about 1.5;
   (b) reducing the alkyl glycolate content by distilling the residue mixture at a lower pressure to provide a residue mixture having an alkyl glycolate/alkyl glyoxylate molar ratio in the range of about 1.0 to about 1.4;
   (c) distilling the residue mixture at increased pressure and recovering high purity alkyl glyoxylate as the distillate.

2. The process of claim 1 wherein the pressure employed in (a) is in the range of about 50 to about 300 torr (6.7–40.0 kPa), the pressure employed in (b) is less than about 35 torr (4.7 kPa) and the pressure employed in (c) is at least about 600 torr (80.0 kPa).

3. The process of claim 2 wherein the pressure employed in (b) is in the range of about 2 to about 22 torr (0.27–2.93 kPa) and the pressure employed in (c) is in the range of about 700 to about 912 torr (93.3–121.6 kPa).

4. The process of claim 1 wherein the alkyl moieties of the alkyl glyoxylate, alkyl glycolate and alcohol are of 1 to 4 carbon atoms.

5. The process of claim 1 wherein the starting mixture has an alkyl glycolate/alkyl glyoxylate molar ratio in the range of about 1.5 to about 2.6.

6. The process of claim 1 wherein the residue mixture of (a) has a combined water and alcohol content of less than about 0.30% by weight.

7. The process of claim 1 wherein the recovered alkyl glyoxylate contains at least about 30 moles of alkyl glyoxylate per mole of water, alcohol and alkyl glycolate combined.

8. A process for production of high purity alkyl glyoxylate from a mixture containing alkyl glyoxylate, alkyl glycolate, water, alcohol and miscellaneous impurities, said mixture having an alkyl glycolate/alkyl glyoxylate molar ratio in the range of about 1.5 to about 2.6, which comprises:
   (a) reducing the water and alcohol content by distilling the mixture at a pressure in the range of from about 50 to about 300 torr (6.7–40.0 kPa) to provide a residue mixture having a combined water and alcohol content of less than about 1% by weight;
   (b) reducing the alkyl glycolate content by distilling the residue mixture at a pressure in the range of about 2 to about 35 torr (0.27–4.7 kPa) to provide a residue mixture having an alkyl glycolate/alkyl glyoxylate molar ratio in the range of about 1.0 to about 1.4;
   (c) distilling the residue mixture of (b) at a pressure in the range of about 600 to about 1550 torr (80.0–206.6 kPa) and recovering the alkyl glyoxylate as the distillate.

9. The process of claim 8 wherein the alkyl moieties of said alkyl glycolate, alkyl glyoxylate and alcohol are the same and are of 1 to 4 carbon atoms.

10. The process of claim 9 wherein the alkyl moieties are methyl.

11. The process of claim 10 wherein the pressure employed in (a) is in the range of about 150 to about 200 torr (20.0–26.7 kPa), the pressure employed in (b) is in the range of about 2 to about 22 torr (0.27 to 2.93 kPa) and the pressure employed in (c) is in the range of about 700 to about 912 torr (93.3–121.6 kPa).

12. The process of claim 11 wherein the recovered alkyl glyoxylate contains at least about 30 moles of alkyl glyoxylate per mole of water, alcohol and alkyl glycolate combined.

13. A process for the production of high purity alkyl glyoxylate from a mixture obtained from the dehydrogenation of alkyl glycolate and containing alkyl glycolate, alkyl glyoxylate, water, alcohol, miscellaneous impurities and added alkyl glycolate to adjust the alkyl glycolate/alkyl glyoxylate molar ratio of the mixture to the range of about 1.5 to about 2.6 which comprises:
   (a) reducing the water and alcohol content by distilling the mixture at a reduced pressure to provide a residue mixture having a combined water and alcohol content of less than about 1% by weight;
   (b) reducing the alkyl glycolate content by distilling the residue mixture at a lower pressure to provide a residue mixture having an alkyl glycolate/alkyl glyoxylate molar ratio in the range of about 1.0 to about 1.4;
   (c) distilling the residue mixture of (b) at an increased pressure and recovering high purity alkyl glyoxylate as the distillate.

14. The process of claim 13 wherein the pressure employed in (a) is in the range of about 50 to about 300 torr (6.7–40.0 kPa), the pressure employed in (b) is in the range of about 2 to about 35 torr (0.27–2.93 kPa) and the pressure employed in (c) is in the range of about 600 to about 1550 torr (80.0–206.6 kPa).

15. The process of claim 13 wherein the pressure employed in (a) is in the range of about 150 to about 200 torr (20.0–26.7 kPa), the pressure employed in (b) is in the range of about 2 to about 22 torr (0.27–2.93 kPa) and the pressure employed in (c) is in the range of about 700 to about 912 torr (93.3–121.6 kPa).

16. The process of claim 15 wherein the alkyl moieties of the alkyl glyoxylate, alkyl glycolate and alcohol are methyl.

17. The process of claim 16 wherein the residue mixture of (a) has a combined water and alcohol content of less than about 0.30% by weight.

18. The process of claim 16 wherein the residue mixture of (b) has a methyl glycolate/methyl glyoxylate molar ratio in the range of about 1.1 to about 1.3.

19. The process of claim 16 wherein the methyl glyoxylate recovered contains at least about 30 moles methyl glyoxylate per mole of water, methyl alcohol and methyl glycolate combined.

20. The process of claim 16 wherein the methyl glyoxylate recovered contains at least about 70 moles methyl glyoxylate per mole of water, methyl alcohol and methyl glycolate combined.

* * * * *